US00PP21390P2

(12) United States Plant Patent
Roberson

(10) Patent No.: US PP21,390 P2
(45) Date of Patent: Oct. 19, 2010

(54) ***BUXUS* PLANT NAMED 'ROBBUXUPT'**

(50) Latin Name: *Buxus microphylla*
Varietal Denomination: Robbuxupt

(76) Inventor: Robert Jackson Roberson, 31706 E Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 12/462,624

(22) Filed: Aug. 5, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
*Assistant Examiner*—Louanne C Krawczewicz Myers

(57) ABSTRACT

A new cultivar of *Buxus microphylla* named 'ROBBUXUPT' that is characterized by upright columnar growth habit, dense branching and deep green foliage which remains evergreen in USDA Zone 5 winters. In combination, these characteristics distinguish 'ROBBUXUPT' from all other existing varieties of *Buxus* known to the inventor.

3 Drawing Sheets

Genus: *Buxus.*
Species: *microphylla*
Denomination: 'ROBBUXUPT'.

BACKGROUND OF THE INVENTION

The present invention relates to a new and distinct cultivar of small-leaved Boxwood grown as an ornamental evergreen shrub for use in the landscape and as a specimen or hedging plant in the garden. The new cultivar is known botanically as *Buxus microphylla* 'ROBBUXUPT' and will be referred to hereinafter by the cultivar name 'ROBBUXUPT'.

'ROBBUXUPT' was discovered in 1989 at the inventor's nursery in Grain Valley, Mo. as a naturally occurring sport which the inventor discovered growing within a commercial crop of *Buxus microphylla* 'Wintergreen' (unpatented). The inventor observed that the new variety, 'ROBBUXUPT', exhibited a distinctive columnar form and bore noticeably darker green foliage than the sport parent variety, 'Wintergreen'. In subsequent years, the inventor observed that 'ROBBUXUPT' remained evergreen through the winter whereas the foliage of 'Wintergreen' loses its green color and turns bronze.

The inventor first asexually propagated 'ROBBUXUPT' in 1990 at the inventor's nursery in Grain Valley, Mo., using tip cuttings. Rooting was successful and the grown-on plants exhibited the characteristic habit and leaf color of the initial discovery. The inventor has determined that the distinguishing characteristics of 'ROBBUXUPT' remain stable and uniform in successive generations of asexual reproduction.

SUMMARY OF THE INVENTION

The following represent the distinguishing characteristics of the new *Buxus microphylla* cultivar 'ROBBUXUPT'. In combination these traits set 'ROBBUXUPT' apart from all other varieties of *Buxus microphylla* known to the inventor. 'ROBBUXUPT' has not been tested under all possible conditions and phenotypic differences may be observed with variations in environmental, climatic, and cultural conditions, however, without any variance in genotype.

1. 'ROBBUXUPT' exhibits an upright or columnar growth habit.
2. 'ROBBUXUPT' exhibits tight, dense branching and leaf structure.
3. The foliage of 'ROBBUXUPT' is deep green in color.
4. 'ROBBUXUPT' is hardy to USDA zone 5.
5. 'ROBBUXUPT' maintains green color through the winter.

BRIEF DESCRIPTION OF THE DRAWINGS

The accompanying color drawings illustrates the overall appearance of an entire plant of the new *Buxus microphylla* cultivar 'ROBBUXUPT' showing the colors as true as it is reasonably possible to obtain in colored reproductions of this type. Colors in the drawings may differ from the color values cited in the detailed botanical description, which accurately describe the actual colors of the new variety 'ROBBUXUPT'. All drawings have been made from plants growing out of doors in the inventor's nursery in Grain Valley, Mo.

The drawing labeled

The drawing labeled

The drawing labeled

BOTANICAL DESCRIPTION OF THE PLANT

Figure 1:
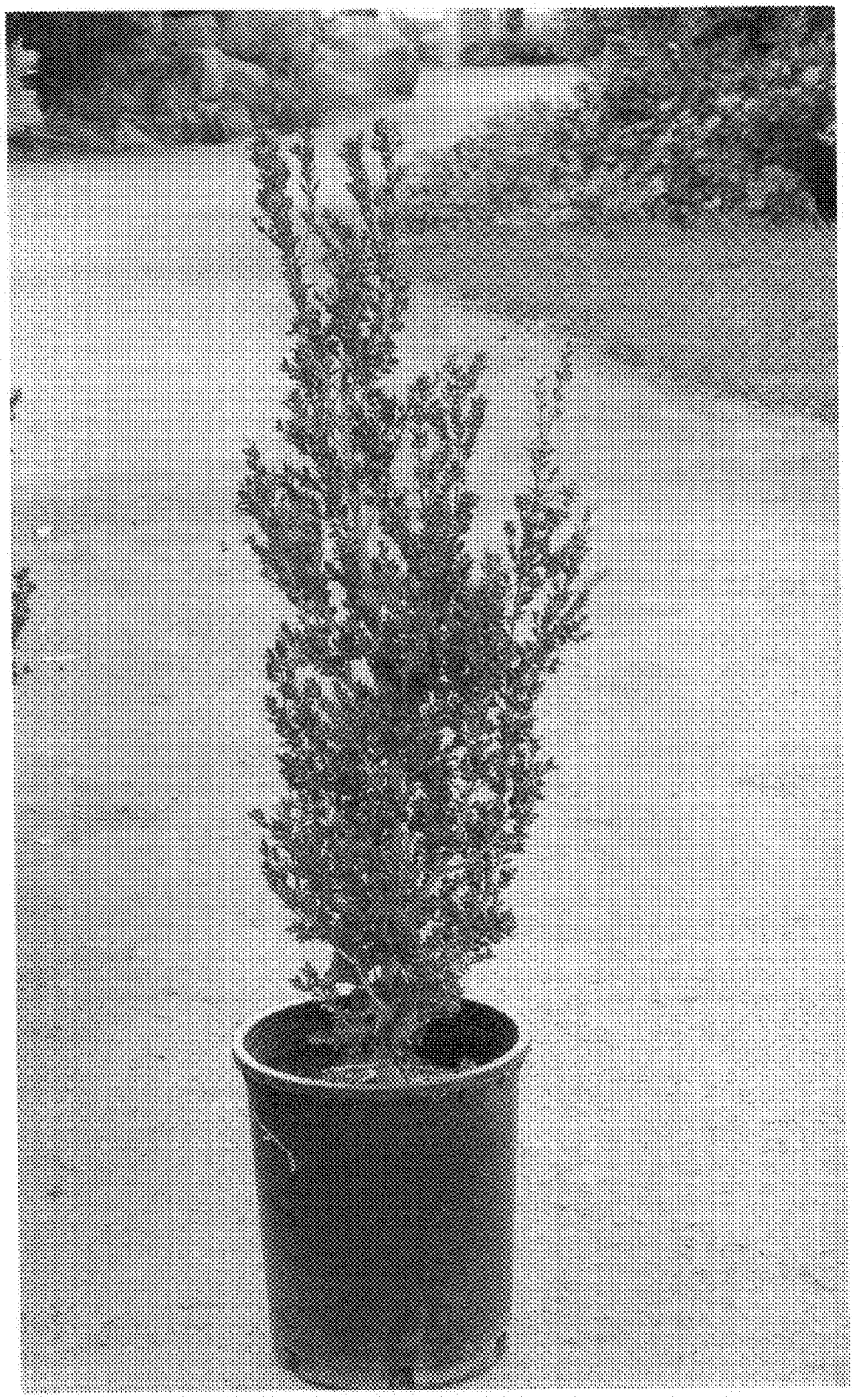
FIG. 1 illustrates a 3 year old plant of 'ROBUXPT' which is growing in a 5 gallon container.
Figure 2:
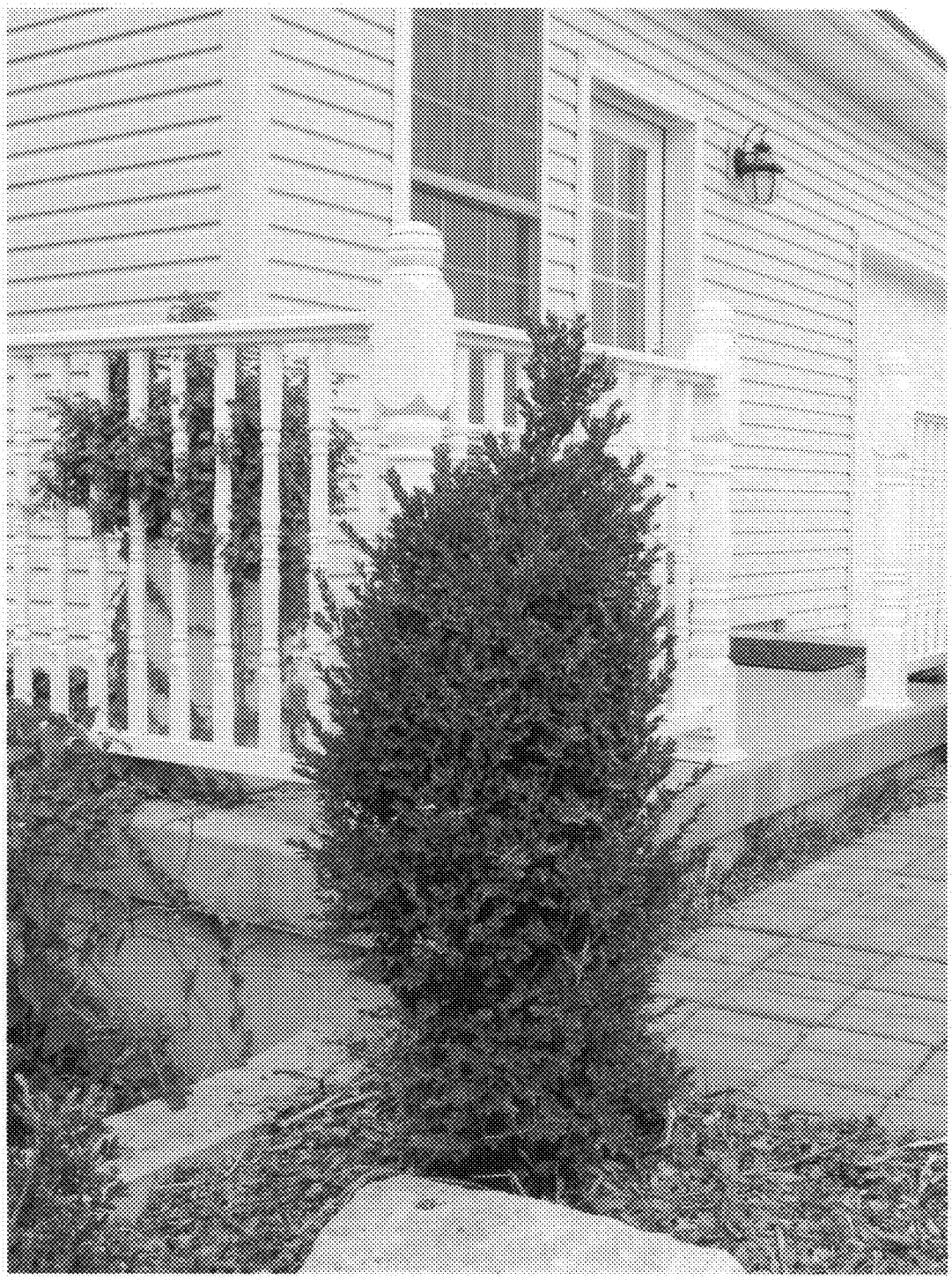
FIG. 2 illustrates a 6 year old plant of 'ROBBUXUPT' which is growing in ground.
Figure 3:
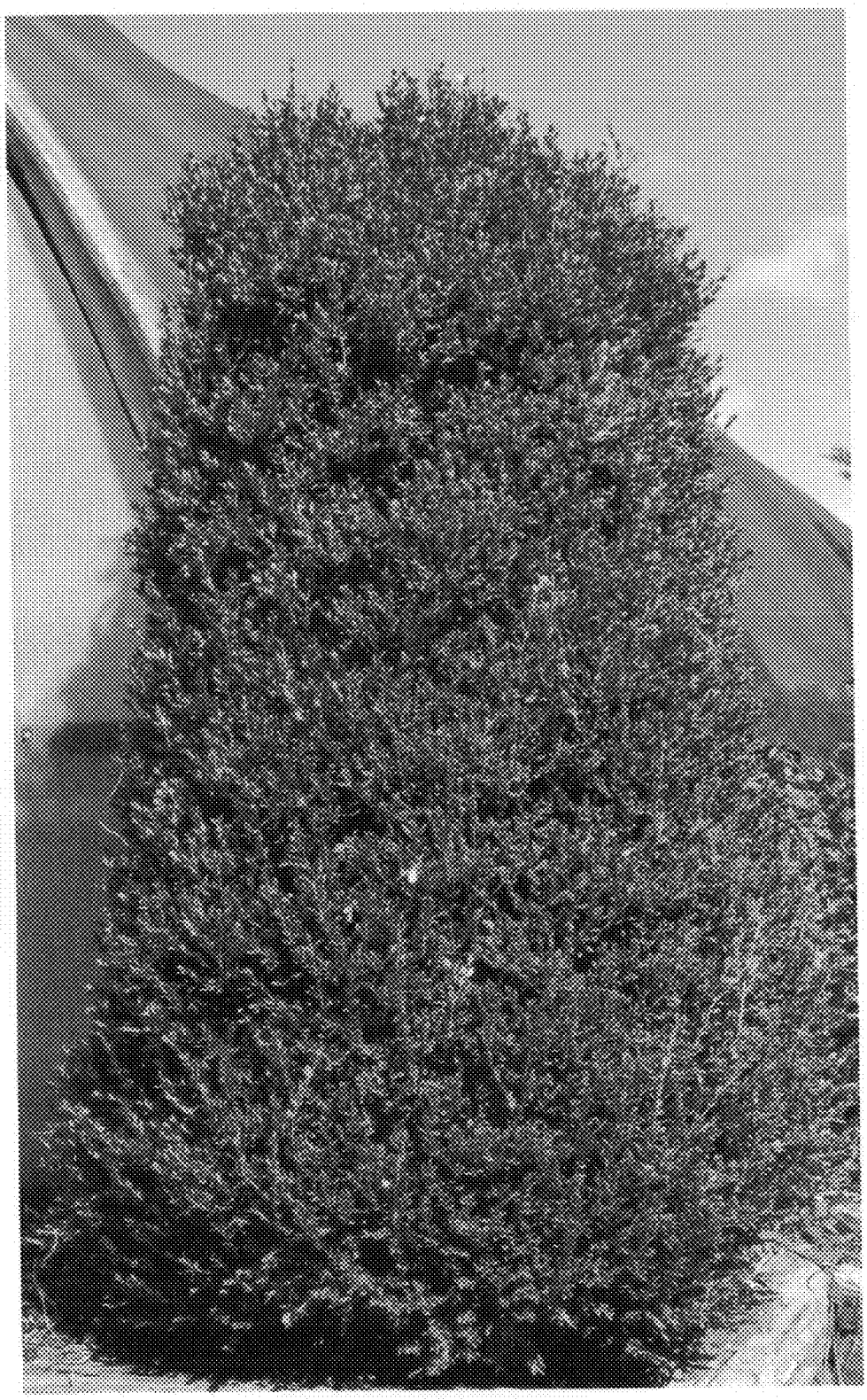
FIG. 3 illustrates the original discovered plant at 18 years of age and growing in-ground.

The following is a detailed description of the *Buxus microphylla* cultivar named 'ROBBUXUPT'. Data was collected from four year old plants growing out of doors, in ground, in Grain Valley, Mo. Color determinations are in accordance with The Royal Horticultural Society Colour Chart, 2007 Edition, except where general color terms of ordinary dictionary significance are used.

Botanical classification: *Buxus microphylla* 'ROBBUXUPT'.

Use: Ornamental landscape plant.

Parent: 'ROBBUXUPT' arose as a naturally occurring sport of *Buxus microphylla* 'Wintergreen' (unpatented).

Type: Evergreen shrub.
Vigor: Medium.
Habit: Upright, columnar.
Height: 81 cm-84 cm after 4 years from initial propagation.
Width: 33 cm-36 cm after 4 years.
Hardiness: USDA Zone 5.
Propagation: Medium hardwood cuttings.
Root system: Fine and fibrous.
Soil: Plant in loam or well drained soil.
Sunlight: Plant in full sunlight.
Production schedule: It is recommended that tip cuttings are taken before spring flush (typically in March), placed on rooting bench with heat for 8-12 weeks, potted into deep liner cells or pots, re-potted into 1 gallon containers for 12 months, then again into 3-5 gallon for 24 months.
Diseases and pests: None known to inventor.
Stems:
*Branching habit.*—Freely branching. No basal branching.
*Number of branches.*—Approximately 150 branches including laterals.
*Internode length.*—1 cm. between nodes, on average.
*Stem diameter.*—4 cm in diameter at the base, reducing to 5 mm in diameter at the apex.
*Stem length of an individual branch.*—25 cm-35 cm.
*Shape.*—Quadrangular.
*Stem surface* (*lignified, mature*).—Rough, coriaceous, color ranges between 161A and 163D.
*Stem surface* (*green, juvenile*).—Smooth, very slightly glossy, color 138B.
*Pubescence.*—Very short (less than 0.1 mm) white hairs at the young growth tips.
Foliage:
*Leaf arrangement.*—Opposite.
*Leaf division.*—Simple.
*Leaf number per lateral branch.*—Average 40 (20 pairs)
*Leaf shape* (*young and mature*).—Ovate to broad elliptic; occasionally obovate.
*Leaf base* (*young and mature*).—Acuminate.
*Leaf apex* (*young and mature*).—Rounded.
*Leaf venation.*—Pinnate.
*Vein color for young and mature leaves.*—Upper surface: 139B. Lower surface: 138C.
*Pubescence.*—None present.
*Margin.*—Entire.
*Leaf surface* (*both surfaces*).—Smooth, leathery, glossy.
*Leaf attachment.*—Petiolate.
*Petiole length.*—1 mm.
*Petiole shape and diameter.*—Flattened: diameter from 1.0 mm to 0.6mm.
*Petiole color.*—138B.
*Petiole surface.*—Smooth.
*Leaf dimensions.*—3-4 mm in width and 7-9 mm in length.
*Leaf color* (*upper surface*).—Between 139A.
*Leaf color* (*lower surface*).—138B.
*Foliar fragrance.*—Slightly pungent, ammoniacal.
Flowers:
*Arrangement.*—Axillary spike with single apical female flower surrounded by 3 to 5 male flowers (the genus *Buxus* is monoecious). Flowers appear in April-May, small, star-shaped, diameter approximately 5 mm, sessile, fragrant.
*Male flower.*—4 tepals, color 155A, 4 stamens around a pistillode, anthers conspicuous, color 9A.
*Female flower.*—4-6 tepals, color 155A.
Fruit: Ovoid, length 4 mm, width 3 mm, color, 137C, flattened apex bearing three stubby horns; dehiscing (at the horns) into three bi-valved capsules.
Seed: 2 per capsule, oblong, 3 mm in length, 1 mm in width, color 202A, shiny.

The invention claimed is:

1. A new and distinct variety of *Buxus microphylla* plant named 'ROBBUXUPT' as described and illustrated.

* * * * *